(12) United States Patent
Babaeizadeh

(10) Patent No.: US 11,123,023 B2
(45) Date of Patent: Sep. 21, 2021

(54) METHOD AND APPARATUS FOR DETERMINING RESPIRATORY INFORMATION FOR A SUBJECT

(71) Applicant: KONINKLIJKE PHILIPS N.V., Eindhoven (NL)

(72) Inventor: Saeed Babaeizadeh, Arlington, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 93 days.

(21) Appl. No.: 16/301,468

(22) PCT Filed: Jun. 20, 2017

(86) PCT No.: PCT/EP2017/065007
§ 371 (c)(1),
(2) Date: Nov. 14, 2018

(87) PCT Pub. No.: WO2017/220526
PCT Pub. Date: Dec. 28, 2017

(65) Prior Publication Data
US 2019/0282180 A1 Sep. 19, 2019

Related U.S. Application Data

(60) Provisional application No. 62/353,102, filed on Jun. 22, 2016.

(30) Foreign Application Priority Data

Jul. 18, 2016 (EP) .................................. 16179941

(51) Int. Cl.
*A61B 5/0205* (2006.01)
*A61B 5/00* (2006.01)
(Continued)

(52) U.S. Cl.
CPC .......... *A61B 5/7278* (2013.01); *A61B 5/0205* (2013.01); *A61B 5/0816* (2013.01);
(Continued)

(58) Field of Classification Search
USPC .................................................. 600/300–301
See application file for complete search history.

(56) References Cited

U.S. PATENT DOCUMENTS

| 5,273,036 A | 12/1993 | Kronberg |
| 5,913,308 A | 6/1999 | Forbes |

(Continued)

FOREIGN PATENT DOCUMENTS

| WO | 2009127799 | 10/2009 |
| WO | 2012052951 | 4/2012 |

(Continued)

OTHER PUBLICATIONS

Schmitz, et al., "Peripheral Vascular Noninvasive Measurements", Encyclopedia of Medical Devices and Instrumentation, Second Edition, edited by John G. Webster, 2006 John Wiley & Sons, Inc.
(Continued)

*Primary Examiner* — Nicole F Lavert

(57) ABSTRACT

There is provided a method and apparatus for determining respiratory information for a subject. One or more physiological signals indicative of at least one physiological characteristic of the subject is acquired (202) and contextual information relating to at least one of the subject and the one or more physiological signals is obtained (204). Based on the contextual information, at least one signal processing algorithm for each of the one or more physiological signals is selected (206), the at least one signal processing algorithm being adapted to determine respiratory information. Respiratory information for the subject is determined based on the one or more physiological signals using the at least one
(Continued)

signal processing algorithm selected for the one or more physiological signals (208).

18 Claims, 8 Drawing Sheets

(51) Int. Cl.
| | |
|---|---|
| A61B 5/08 | (2006.01) |
| A61B 5/024 | (2006.01) |
| A61B 5/113 | (2006.01) |
| A61B 5/1455 | (2006.01) |
| A61B 5/0535 | (2021.01) |
| A61B 5/349 | (2021.01) |
| A61B 5/364 | (2021.01) |
| A61B 5/366 | (2021.01) |
| A61B 5/389 | (2021.01) |

(52) U.S. Cl.
CPC .......... *A61B 5/7203* (2013.01); *A61B 5/7207* (2013.01); *A61B 5/7221* (2013.01); *A61B 5/7235* (2013.01); *A61B 5/02405* (2013.01); *A61B 5/02416* (2013.01); *A61B 5/0535* (2013.01); *A61B 5/0809* (2013.01); *A61B 5/113* (2013.01); *A61B 5/14552* (2013.01); *A61B 5/349* (2021.01); *A61B 5/364* (2021.01); *A61B 5/366* (2021.01); *A61B 5/389* (2021.01); *A61B 2560/0431* (2013.01); *A61B 2562/0219* (2013.01)

(56) References Cited

U.S. PATENT DOCUMENTS

| | | |
|---|---|---|
| 8,758,243 B2 | 6/2014 | Wang |
| 2003/0055348 A1 | 3/2003 | Chazal |
| 2005/0209521 A1 | 9/2005 | Kettunen |
| 2006/0041201 A1 | 2/2006 | Behbehani |
| 2010/0069762 A1 | 3/2010 | Mietus |
| 2013/0116520 A1 | 5/2013 | Roham |
| 2015/0313484 A1 | 11/2015 | Burg |
| 2016/0007935 A1* | 1/2016 | Hernandez .......... A61B 5/6814 600/301 |
| 2016/0051205 A1 | 2/2016 | Al-Ali |
| 2016/0067433 A1 | 3/2016 | Martin |

FOREIGN PATENT DOCUMENTS

| | | |
|---|---|---|
| WO | 2013140324 | 9/2013 |
| WO | 2015175904 | 11/2015 |

OTHER PUBLICATIONS

John Allen, "Photoplethysmography and its application in clinical physiological measurement", Physiol. Meas. 28 (2007) R1-R39.

Moody, et al., "Derivation of respiratory signals from multi-lead ECGs", Computers in cardiology, Jan. 1985.

Helfenbein, et al., "Development of three methods for extracting respiration from the surface ECG: a review", Journal of Electrocardiology 47 (2014) 819-825.

Babaeizadeh, et al., "Improvements in atrial fibrillation detection for real-time monitoring", Journal of Electrocardiology 42 (2009) 522-526.

Frank, "An accurate, clinically practical system for spatial vectorcardiography", Circulation, vol. XIII, May 1956.

Bailón, et al., "ECG Derived Respiratory Frequency Estimation—Chapter 8", Advanced Methods and Tools for ECG Data Analysis, 2006.

Chan, et al,. "Ambulatory Respiratory Rate Detection using ECG and a Triaxial Accelerometer", 35th Annual International Conference of the IEEE EMBS, Osaka, Japan, Jul. 3-7, 2013.

Nemati, et al., "Data Fusion for Improved Respiration Rate Estimation", EURASIP J Adv Signal Process. 2010.

* cited by examiner

METHOD AND APPARATUS FOR DETERMINING RESPIRATORY INFORMATION FOR A SUBJECT

CROSS REFERENCE TO RELATED APPLICATIONS

This application is the U.S. National Phase application under 35 U.S.C. § 371 of International Application No. PCT/EP2017/065007, filed Jun. 20, 2017 published as WO 2017/220526 on Dec. 28, 2017, which claims the benefit of European Patent Application Number 16179941.6 filed Jul. 18, 2016 and U.S. Provisional Patent Application No. 62/353,102 filed Jun. 22, 2016. These applications are hereby incorporated by reference herein.

TECHNICAL FIELD OF THE INVENTION

The invention relates to a method and apparatus for determining respiratory information for a subject.

BACKGROUND TO THE INVENTION

Physiological monitoring of respiratory activity is important in many clinical settings, including critical and neonatal care, sleep study assessment and anaesthetics. While satisfactory measurement methods have been provided for incubated subjects or subjects wearing a breathing mask, issues still exist with the non-invasive monitoring of respiration, such as issues relating to the operation, reliability, accuracy and repeatability of measurements. For example, respiration sensors based on a thermistor in the respiratory path in front of the mouth and/or nose of a subject are difficult to apply and are frequently not tolerated by the subject. Also, breathing belts around the chest and abdomen of a subject for mechanical pulmonary plethysmography require a great deal of care, additional wires on the subject and monitoring devices.

Several methods exist for non-invasive monitoring of respiration that create fewer disturbances to the subject. For example, impedance-pneumography is a commonly-used technique to monitor respiration. This method usually employs two electrocardiogram (ECG) chest electrodes to monitor respiration by measuring the modulation of the thorax impedance due to respiration. However, this weak respiration signal is subject to a base line drift (which is a function of the position of the body), and interference from local electrode skin transition impedances. Moreover, aside from using regular ECG electrodes, satisfactory monitoring of respiration can generally only be achieved with additional electrodes attached to the subject and using four-conductor measurement technology. A fundamental disadvantage of this measurement method is that a measurable respiratory movement is not a sign of effective respiration. For example, there may be obstructions in the respiratory path or unco-ordinated, out-of-phase chest and abdominal respiration. This is particularly an issue in premature infants with respiratory systems that have not fully developed.

Respiration can also be measured from photoplethysmography (PPG). It is possible to monitor breathing using a PPG sensor attached to the skin since respiration causes variation in the peripheral circulation. The low frequency respiratory induced intensity variations in the PPG signal include contributions from the venous return to the heart caused by alterations in intra-thoracic pressure and also changes in the sympathetic tone control of cutaneous blood vessels during respiration. However, PPG signals recorded on the skin are highly sensitive to motion. Furthermore, the analysis of respiratory-induced variations in the PPG waveform usually requires frequency analysis of the PPG baseline in frequency bands that are often filtered out by commercial devices.

Several signal processing algorithms have been developed to extract respiration information from an ECG using regular electrodes (which can be referred to as ECG-derived respiratory (EDR) information). Some methods are based on respiration-induced variations in beat-to-beat ECG morphology (which can be referred to as QRS-EDR). These methods look at the beat-to-beat change in an R-peak amplitude, RS-range, or vectorcardiogram (VCG). Other methods attempt to extract respiratory information for the heart rate (HR) as a result of respiration modulation of HR (which can be referred to as HRV). Also, signal processing algorithms to extract and process electromyogram (EMG) from an ECG can also provide respiration information (which is referred to as EMG-EDR). The premise is that ECG recordings will contain muscle tremor "noise" from electrical activation of the inter-costal chest muscles and the diaphragm during the respiration cycle. However, all of these methods come with advantages and disadvantages for different applications.

For example, while bedside multi-parameter monitors are widely used in patient monitoring, and many vital signals recorded from different sensors can be used to derive respiratory information, it is highly likely that a single recording could fail to continuously generate robust and accurate respiratory information because of certain technical issues (for example, poor signal quality) or certain physiological limitations. Furthermore, a wearable patient monitor may not record all vital signals due to the trade-off in design for portability and low-power consumption (for example, an impedance recording may not be available).

Even in a single physical recording, different signal processing algorithms have advantages and disadvantages because of the basic physical or physiological assumptions. For example, it is not possible to use the HRV-EDR method for subjects with a degenerative nervous system (such as elderly, critically ill, and those with diseases causing autonomic neuropathy). However, the HRV-EDR method has advantages when ECG is recorded on a short electric vector (for example, on patch-like wearable device where two ECG electrodes are very closely placed). Meanwhile, the EMG-EDR method in general can provide better performance since it measures the mechanical respiratory activity. However, the EMG-EDR method has certain hardware requirements for ECG recording (such as high frequency bandwidth and sampling rate, which increases both the cost and power usage of the device).

Therefore, there is a need for an improved method and apparatus for determining respiratory information for a subject.

SUMMARY OF THE INVENTION

As noted above, a limitation with existing techniques for determining respiratory information is that there is no single method that is suitable in every situation or that provides optimum results in every situation.

Therefore, according to a first aspect of the invention, there is provided a method for determining respiratory information for a subject. The method comprises acquiring one or more physiological signals indicative of at least one physiological characteristic of the subject, obtaining contextual information relating to at least one of the subject and the one or more physiological signals. The method also comprises selecting, based on the contextual information, at least one signal processing algorithm for each of the one or more physiological signals, the at least one signal processing algorithm being adapted to determine respiratory information. The method also comprises determining respiratory information for the subject based on the one or more physiological signals using the at least one signal processing algorithm selected for the one or more physiological signals.

In some embodiments, the one or more physiological signals for which at least one signal processing algorithm is selected may be one or more physiological signals selected based on the contextual information relating to the one or more physiological signals.

In some embodiments, two or more signal processing algorithms may be selected for at least one physiological signal and the method may further comprise combining the two or more signal processing algorithms selected for the at least one physiological signal into a combined signal processing algorithm and determining respiratory information for the subject based on the at least one physiological signal using the combined signal processing algorithm for the at least one physiological signal.

In some embodiments, two or more physiological signals may be acquired and the method may further comprise combining the respiratory information that is determined from each of the two or more physiological signals.

In some embodiments, the method may further comprise, prior to determining respiratory information for the subject, filtering the one or more physiological signals to remove noise.

In some embodiments, the respiratory information may comprise at least one of a respiration rate for the subject and a breathing pattern for the subject.

In some embodiments, the at least one signal processing algorithm selected for the physiological signal may comprise one or more of: a frequency domain analysis of the physiological signal, a time domain analysis of the physiological signal, and an auto-regression analysis of the physiological signal.

In some embodiments, the method may further comprise outputting the determined respiratory information for the subject.

In some embodiments, the method may further comprise determining a respiratory condition for the subject based on the determined respiratory information for the subject.

In some embodiments, the method may further comprise outputting the determined respiratory condition for the subject.

According to a second aspect of the invention, there is provided a computer program product comprising a computer readable medium, the computer readable medium having computer readable code embodied therein, the computer readable code being configured such that, on execution by a suitable computer or processor, the computer or processor is caused to perform the method or the methods described above.

According to a third aspect of the invention, there is provided an apparatus for determining respiratory information for a subject. The apparatus comprises a control unit configured to acquire one or more physiological signals indicative of at least one physiological characteristic of the subject and obtain contextual information relating to at least one of the subject and the one or more physiological signals. The control unit is also configured to select, based on the contextual information, at least one signal processing algorithm for each of the one or more physiological signals, the at least one signal processing algorithm being adapted to determine respiratory information. The control unit is also configured to determine respiratory information for the subject based on the one or more physiological signals using the at least one signal processing algorithm selected for the one or more physiological signals.

In some embodiments, the control unit may be configured to acquire the one or more physiological signals by controlling one or more physiological sensors to acquire the one or more physiological signals.

In some embodiments, the one or more physiological sensors may comprise at least one of: an electrocardiogram sensor, an impedance sensor, an acceleration sensor, and a photoplethysmography sensor.

In some embodiments, a wearable device may comprise the one or more physiological sensors.

In this way, the limitations of existing techniques are addressed. According to the above aspects and embodiments, there is provided a method for automatic selection of different signal processing algorithms to derive respiratory information from one or more physiological signals in a manner that improves the overall performance and can deal with different clinical conditions for monitoring respiratory activity.

There is thus provided an improved method and apparatus for determining respiratory information for a subject, which overcomes the existing problems.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

As noted above, the invention provides an improved method and apparatus for determining respiratory information for a subject, which overcomes the existing problems.

Figure 1:
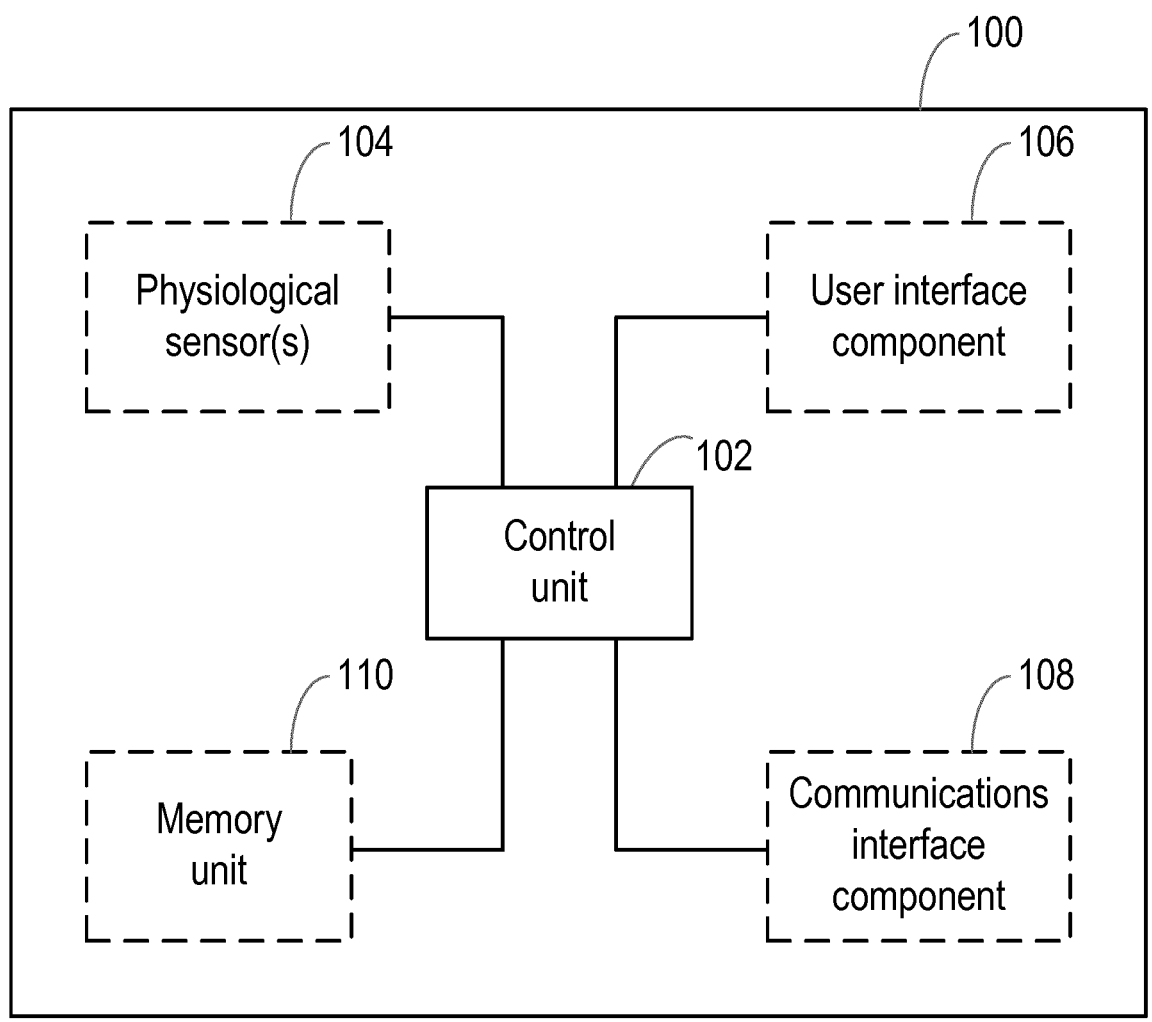
FIG. 1 is a block diagram of an apparatus according to an embodiment.

FIG. 1 shows a block diagram of an apparatus 100 according to an embodiment of the invention that can be used for determining respiratory information for a subject. A subject may be a patient or any other subject or user of the apparatus 100.

The apparatus 100 comprises a control unit 102 that controls the operation of the apparatus 100 and that can implement the method described herein. The control unit 102 can comprise one or more processors, processing units, multi-core processors or modules that are configured or programmed to control the apparatus 100 in the manner described herein. In particular implementations, the control unit 102 can comprise a plurality of software and/or hardware modules that are each configured to perform, or are for performing, individual or multiple steps of the method according to embodiments of the invention.

Briefly, the control unit 102 is configured to acquire one or more physiological signals indicative of at least one physiological characteristic of the subject and obtain contextual information relating to at least one of the subject and the one or more physiological signals. The control unit 102 is further configured to select, based on the contextual information, at least one signal processing algorithm for each of the one or more physiological signals, the at least one signal processing algorithm being adapted to determine respiratory information. The control unit 102 is also configured to determine respiratory information for the subject based on the one or more physiological signals using the at least one signal processing algorithm selected for the one or more physiological signals.

In some embodiments, the control unit 102 is configured to acquire the one or more physiological signals (or vital sign signals) by controlling one or more physiological sensors 104 to acquire the one or more physiological signals. In the illustrated embodiment of FIG. 1, the apparatus comprises one or more physiological sensors 104. However, it will be understood that one or more physiological sensors may alternatively or additionally be external to (i.e. separate to or remote from) the apparatus 100. In some embodiments, a wearable device can comprise the one or more physiological sensors. In some embodiments, the apparatus 100 comprising the control unit 102 and one or more physiological sensors 104 may be a wearable device. The wearable device may be in the form of a watch, a necklace, a patch, a band for a part of the body, or any other device designed to be worn by a subject.

The one or more physiological sensors can comprise at least one of an electrocardiogram (ECG) sensor, an impedance sensor, an acceleration sensor (such as an accelerometer), a photoplethysmography (PPG) sensor (such as a pulse oximeter), or any other physiological sensors, or combination of physiological sensors suitable for acquiring a physiological signal indicative of at least one physiological characteristic of the subject.

The physiological signal indicative of at least one physiological characteristic of the subject acquired from an ECG sensor is an electrocardiogram signal. An ECG sensor may comprise one or more electrodes. The physiological signal indicative of at least one physiological characteristic of the subject acquired from a PPG sensor (such as a pulse oximeter) is a photoplethysmography signal. A PPG sensor may comprise one or more light sources (for example, light emitting diodes, LEDs) operating at specific frequencies and one or more light detectors (for example, photo-diodes), which react to the light that is either reflected or transmitted when the PPG sensor is in contact with the skin of the subject. The physiological signal indicative of at least one physiological characteristic of the subject acquired from an impedance sensor is an impedance signal. An impedance sensor may be a bio-impedance sensor that is operable to measure a resistance of the bio-tissue of the subject to an electric current or to an electric voltage. For example, at least one electrode may drive electric energy into the bio-tissue of the subject and at least one electrode may detect changes in voltage. Alternatively, at least one electrode may apply electric voltage on the bio-tissue of the subject and at least one electrode may detect changes in corresponding electric current. The physiological signal indicative of at least one physiological characteristic of the subject acquired from an acceleration sensor (such as an accelerometer) is an acceleration signal.

Although examples have been provided for the one or more physiological sensors, those skilled in the art will be aware of other types of physiological sensors and combinations of physiological sensors.

Returning again to FIG. 1, in some embodiments, the apparatus 100 may also comprise at least one user interface component 106. Alternatively or in addition, a user interface component 106 may be external to (i.e. separate to or remote from) the apparatus 100. For example, the user interface component 106 may be part of another device.

A user interface component 106 may be for use in providing the subject or other user of the apparatus 100 (for example, a healthcare provider, a healthcare specialist, a care giver, or any other person) with information resulting from the method according to the invention. The control unit 102 may be configured to control one or more user interface components 106 to provide information resulting from the method according to the invention. For example, the control unit 102 may be configured to control one or more user interface components 106 to render the determined respiratory information for the subject or any other information determined by the methods described herein. Alternatively or in addition, a user interface component 106 may be configured to receive a user input. In other words, a user interface component 106 may allow a subject or another user of the apparatus 100 to manually enter data, instructions, or information. The control unit 102 may be configured to acquire a user input from one or more user interface components 106.

A user interface component 106 may be or may comprise any component that enables rendering or output of information, data or signals to the subject or another user of the apparatus 100. Alternatively or in addition, a user interface component 106 may be or may comprise any component that enables the subject or another user of the apparatus 100 to provide a user input, interact with and/or control the apparatus 100. For example, the user interface component 106 may comprise one or more switches, one or more buttons, a keypad, a keyboard, a touch screen or an application (for example, on a tablet or smartphone), a display screen or other visual indicator, one or more speakers, one or more microphones, any other voice dialogue components, one or more lights, a component for providing tactile feedback (for example, a vibration function), or any other user input component or combination of user interface components.

In some embodiments, the apparatus 100 may also comprise a communications interface component 108 for enabling the apparatus 100 to communicate with any components, units, sensors and devices that are internal or external to the apparatus 100. The communications interface component 108 may communicate with any components, units, sensors and devices wirelessly or via a wired connection. For example, in the embodiment where the user interface component 106 is external to the apparatus 100, the communications interface component 108 may communicate with the external user interface component wirelessly or via a wired connection.

In some embodiments, the apparatus 100 may also comprise a memory unit 110 configured to store program code that can be executed by the control unit 102 to perform the method described herein. The memory unit 110 can also be used to store information, data, signals and measurements made or acquired by the control unit 102 of the apparatus 100 or by components, units, sensors and devices that are external to the apparatus 100.

It will be appreciated that FIG. 1 only shows the components required to illustrate this aspect of the invention, and in a practical implementation the apparatus 100 may comprise additional components to those shown. For example, the apparatus 100 may comprise a battery or other power supply for powering the apparatus 100 or means for connecting the apparatus 100 to a mains power supply.

Figure 2:
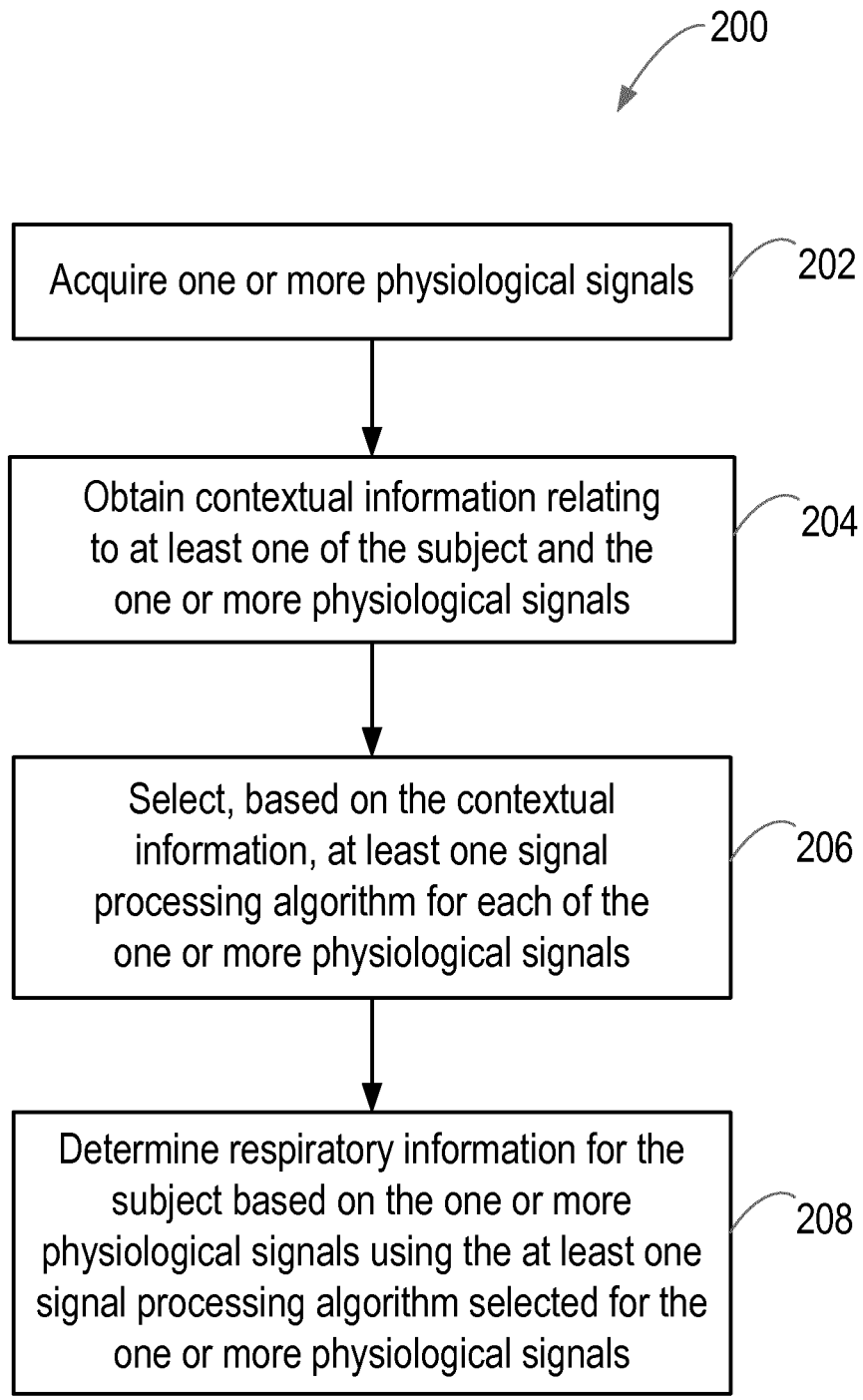
FIG. 2 is a flow chart illustrating a method according to an embodiment.

FIG. 2 illustrates a method 200 for determining respiratory information for a subject according to an embodiment. The illustrated method 200 can generally be performed by or under the control of the control unit 102 of the apparatus 100.

With reference to FIG. 2, at block 202, one or more physiological signals indicative of at least one physiological characteristic of the subject are acquired. As described earlier, the control unit 102 may be configured to acquire the one or more physiological signals by controlling one or more physiological sensors 104 of the apparatus and, alternatively or in addition, one or more physiological sensors external to (i.e. separate to or remote from) the apparatus 100 to acquire the one or more physiological signals.

At block 204, contextual information relating to at least one of the subject and the one or more physiological signals is obtained. In other words, contextual information may be obtained that relates to the subject, or to the one or more physiological signals, or to both the subject and the one or more physiological signals.

The contextual information relating to the subject may be obtained by the control unit 102 from any one of, or any combination of, the user interface component 106 (for example, the contextual information may be in the form of a user input received at the user interface component 106), the memory unit 110 (for example, the contextual information may be stored contextual information), and the communications interface component 108 (for example, the contextual information may be received from a component or unit external to the apparatus 100).

Examples of contextual information relating to the subject include a medical history for the subject, a current medical treatment for the subject, a clinical report for the subject, or any other contextual information relating to the subject, or combination of contextual information relating to the subject. In some examples, a medical history for the subject can include an indication of any disease or condition that the subject has currently or has had in the past. For example, this may be a disease or condition that can potentially lead to one or more medical complications (such as a degenerate nervous system). In some examples, a current medical treatment for the subject may be a medical treatment that can potentially lead to one or more medical complications (such as a treatment that can degenerate the nervous system). In some examples, a clinical report for the subject can be an ECG report (which may, for example, include an indication of whether the subject has a pacemaker, an abnormal heart rhythm, frequent ectopic beats, or similar), a blood test report, a medical imaging report, or any other clinical report, or combination of clinical reports.

Examples of the contextual information relating to the one or more physiological signals include an indication of the quality of the one or more physiological signals (such as a quality index, a quality figure, a signal-to-noise ratio, or any other figure of merit or quality indicator), a sample rate for the one or more physiological signals, information relating to the sensors from which the one or more physiological signals are acquired (such as the availability of the sensors, configuration information for the sensors, or any other information relating to the sensors), or any other contextual information relating to the one or more physiological signals, or combination of contextual information relating to the one or more physiological signals.

Although examples have been provided for the contextual information relating to the subject and for the contextual information relating to the one or more physiological signals, it will be understood that the contextual information can include other contextual information relating to the subject or to the one or more physiological signals or any combination of contextual information.

Returning again to FIG. 2, at block 206, at least one signal processing algorithm for each of the one or more physiological signals is selected based on the contextual information. The selection of at least one signal processing algorithm is automatic. The selected at least one signal processing algorithm is an algorithm that is adapted to determine respiratory information. The at least one signal processing algorithm selected for the physiological signal may comprise a frequency domain analysis of a physiological signal, a time domain analysis of a physiological signal, an auto-regression analysis of the physiological signal, or any other analysis of a physiological signal suitable to determine respiratory information.

Examples of signal processing algorithms include an impedance signal processing algorithm (which may be any algorithm suitable for determining respiratory information from an impedance signal), an accelerometer signal processing algorithm (which may be any algorithm suitable for determining respiratory information from an accelerometer signal), a PPG signal processing algorithm (which may be any algorithm suitable for determining respiratory information from a PPG signal) and an ECG signal processing algorithm (which may be any algorithm suitable for determining respiratory information from an ECG signal). The respiratory information determined using an ECG signal processing algorithm may be referred to as ECG-derived respiratory (EDR) information.

An ECG signal processing algorithm may involve detection of a QRS complex (which may be referred to as a QRS-EDR signal processing algorithm), detection of a QRS complex and an R-peak in the ECG signal (which may be referred to as an R-peak QRS-EDR signal processing algorithm), detection of a QRS complex and determination of an RS-range in the ECG signal (which may be referred to as an RS-range QRS-EDR signal processing algorithm), detection of a QRS complex and a vectorcardiogram VCG analysis (which may be referred to as a VCG QRS-EDR signal processing algorithm), a determination of a heart rate variability HRV (which may be referred to as a HRV-EDR signal processing algorithm), an electromyography EMG analysis (which may be referred to as an EMG-EDR signal processing algorithm), or any signal processing algorithm, or combination of signal processing algorithms suitable for determining respiratory information from an ECG signal. Here, an RS-range is an amplitude difference between an R-wave and an S-wave.

The selection of signal processing algorithms can be based on a set of rules that relate to the advantages and disadvantages of each signal processing algorithms. The set of rules may be stored in the memory unit 110 of the apparatus 100 or an external memory unit accessible by the control unit 102 (such as via the communications interface component 108). The set of rules can be used to exclude signal processing algorithms from selection and, similarly, can be used to include signal processing algorithms for selection. The exclusion of signal processing algorithms may be specific to a certain situation, application, or event indicated by the contextual information.

An example of a set of rules for excluding certain signal processing algorithms for certain situations is provided in the table below:

| Situation | Algorithm | | | | | | | |
|---|---|---|---|---|---|---|---|---|
| | Impedance | Accelerator | PPG | EMG-EDR | HRV-EDR | R-peak QRS-EDR | RS-range QRS-EDR | VCG QRS-EDR |
| Degenerate nervous system | | | | | Exclude | | | |
| Medical treatment that causes degenerate nervous system | | | | | Exclude | | | |
| Paced/irregular heart rhythm | | | | | Exclude | | | |
| Frequent ectopic heart beats | | | Exclude | | Exclude | Exclude | Exclude | Exclude |
| ECG filtering high-frequency cut-off <250 Hz | | | | Exclude | | | | |
| Single-channel ECG | | | | | | | | Exclude |
| Short-vector ECG (wearable patch device) | | | | | | Exclude | Exclude | Exclude |
| Poor/unavailable signal | Exclude | Exclude | Exclude | Exclude | Exclude | Exclude | Exclude | Exclude |

The signal processing algorithms that are not excluded (i.e. that are included) can then be selected for one or more physiological signals based on the contextual information.

Although an example set of rules for excluding certain signal processing algorithms for certain situations has been provided, it will be understood that other signal processing algorithms, other situations and rules for excluding (or including) signal processing algorithm in certain situations can also be used.

According to some embodiments, the one or more physiological signals for which at least one signal processing algorithm is selected are one or more physiological signals selected based on the contextual information relating to the one or more physiological signals. For example, prior to selecting at least one signal processing algorithm for each of the one or more physiological signals at block 206, the method can comprise selecting one or more of the acquired physiological signals based on the contextual information and then, at block 206, at least one signal processing algorithm is selected for each physiological signal that is selected based on the contextual information. In other words, in some embodiments, one or more of the acquired physiological signals may be discarded or excluded from subsequent processing. For example, an acquired physiological signal may be discarded or excluded from subsequent processing if the contextual information includes an indication that the quality of the acquired physiological signal is below a predefined threshold value for signal quality. In this way, it is possible to select optimal physiological signals to be used for subsequent processing.

Returning again to FIG. 2, at block 208, respiratory information for the subject is determined based on the one or more physiological signals using the at least one signal processing algorithm selected for the one or more physiological signals. In some embodiments, prior to determining respiratory information for the subject, the one or more physiological signals may be filtered to remove noise. In these embodiments, subsequent processing is performed using the filtered one or more physiological signals.

The respiratory information that is determined for the subject may comprise at least one of a respiration waveform, a respiration rate for the subject and a breathing pattern for the subject. For example, the respiratory information may comprise a respiration waveform for the subject, a respiration rate for the subject, or a breathing pattern for the subject, or any combination of this respiratory information. Although examples have been provided for the respiratory information that may be determined for the subject, it will be understood that other respiratory information and other combinations of respiratory information are also possible.

In some embodiments, the determined respiratory information for the subject is output. Optionally, a respiratory condition (or a breathing disorder) for the subject may be determined based on the determined respiratory information for the subject. Examples of respiratory condition include sleep-disordered breathing (such as upper airway resistance syndrome and sleep apnea), asthma, bronchitis, and chronic obstructive pulmonary disease (COPD), or any other respiratory condition. In some embodiments, the determined respiratory condition for the subject is output in addition or alternatively to output of the respiratory information. The determined respiratory information for the subject and, alternatively or in addition, the determined respiratory condition for the subject is output via (or rendered by) at least one user interface component 106, which may be part of the apparatus 100 or external to the apparatus 100, as described earlier. In one embodiment, the user interface component 106 is a screen and the output is rendered as an output message on the screen. An output may be rendered during continuous monitoring of the subject or in a retrospective diagnostic report.

As different types of physiological signals may be acquired, different signal processing algorithms may be needed to determine respiratory information (and optionally respiratory conditions) based on these different types of physiological signals. In some embodiments, an ECG signal processing algorithm is used to detect characteristics in the ECG signal. The characteristics can include, for example, a QRS complex, a detected heart beat, a location of an R peak, or any other characteristic in the ECG signal. The ECG signal may be processed in segments (such as 20 second segments, 25 second segments, 30 second segments, 35 second segments, 40 second segments, or any or other size of segment). For example, for each segment of the ECG signal, if there are less than a threshold value of interference-free (or artefact-free) heart beats detected in the segment or if there are more than a threshold value of heart beats that are abnormal (for example, ectopic heart beats), the segment may be discarded.

For each heart beat that is detected in the ECG signal, at least one beat morphology measurements may be determined. For example, a beat morphology measurement may include measurement of an amplitude of an R-wave, measurement of an amplitude of an S-wave, measurement of an RS range, or any other beat morphology measurement, or combination of beat morphology measurements. In this exemplary embodiment, different respiratory information can be determined depending on the different signal processing algorithms that are used to determine the respiratory information. For example, the respiratory information may be determined based on the R-peak QRS-EDR signal processing algorithm, the RS-range QRS-EDR signal processing algorithm, the VCG QRS-EDR signal processing algorithm, the HRV-EDR signal processing algorithm, or the EMG-EDR signal processing algorithm, which were mentioned earlier, or any other signal processing algorithm, or combination of signal processing algorithms suitable for determining respiratory information from an ECG signal. In an embodiment involving an R-peak QRS-EDR signalling processing algorithm, an RS-range QRS-EDR signal processing algorithm, a HRV-EDR signal processing algorithm and an EMG-EDR signal processing algorithm, the ECG signal may be acquired from one or more single-channel ECG sensors. In an embodiment involving a VCG QRS-EDR signal processing algorithm, the ECG signal may be acquired from one or more multi-channel ECG sensors.

The embodiments involving an R-peak QRS-EDR signal processing algorithm, an RS-range QRS-EDR signal processing algorithm, and a HRV-EDR signal processing algorithm may use a similar signal processing algorithm for determining the respiratory information (i.e. for determining the EDR information). For example, for an embodiment involving an R-peak QRS-EDR signal processing algorithm, if there are less than a threshold value of interference-free (or artefact-free) heart beats detected in a segment, the segment may be discarded or if there are more than a threshold value of heart beats that are abnormal (for example, ectopic heart beats). Then, for each segment that remains, an R-wave amplitude is extracted from each heart beat. If the time series for the R-wave amplitude are unevenly sampled, a B-spline interpolation (or any other interpolation techniques) may be used to generate an evenly sampled EGG signal. The ECG signal may be sampled at any suitable rate. For example, the ECG signal may be sampled at a sample rate of 6 samples-per-second, 7 samples-per-second, 8 samples-per-second, 9 samples-per-second, 10 samples-per-second, or any other sample rate. The ECG signal may also be passed through a filter (such as a band-pass filter) to remove sampling aliasing effects that may occur as well as other low frequency and high frequency noise. The filter may correspond to a breathing rate of 8-30 bpm, or similar.

Figure 3:
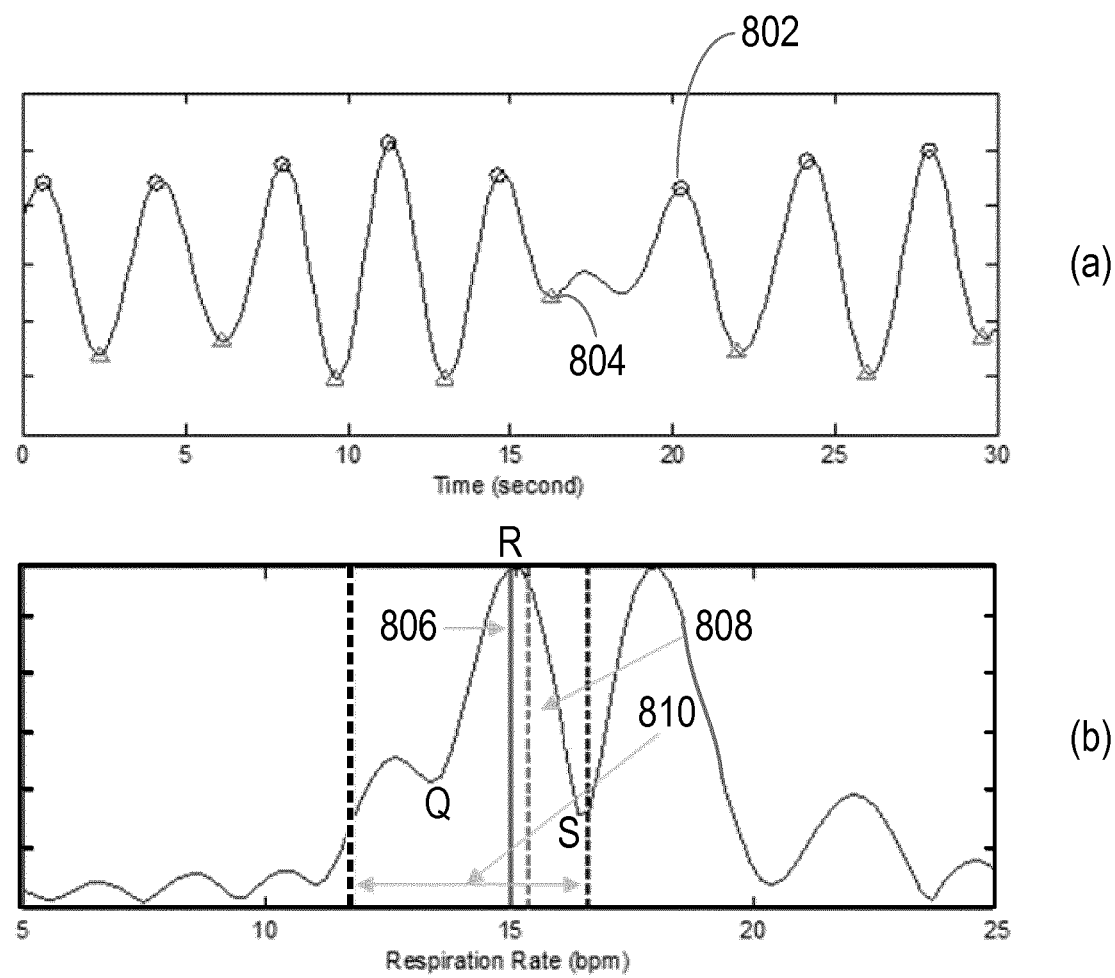
FIG. 3 is a graphical illustration of an exemplary embodiment for determining respiratory information.

FIG. 3 is a graphical illustration of an exemplary embodiment for determining respiratory information based on a physiological signal. Specifically, according to this exemplary embodiment, respiratory information is determined based on an acquired ECG signal using an R-peak QRS-EDR signal processing algorithm.

In the exemplary embodiment illustrated in FIG. 3, a time-frequency domain method is used to process the ECG signal. In this method, peaks and troughs are first detected in the ECG signal in time domain in order to estimate the respiration rate. FIG. 3($a$) illustrates a 30 second segment of an ECG signal in which peaks 802 and troughs 804 are detected in the time-domain. The respiration rate can be determined as the inverse of the average of each valid peak-to-peak and trough-to-trough interval. In more detail, for the exemplary embodiment, in the 30 second segment the peak-to-peak and trough-to-trough intervals are detected and a vector of instantaneous respiration rates (IRRs) is determined as the inverse of the detected peak-to-peak and trough-to-trough intervals. Optionally, a determined IRR may be marked as invalid if the IRR is above a predefined value (for example, 6 bpm) and is at least 30% more than the previous IRR and, alternatively or additionally, if the IRR is at least 40% more than the IRR that precedes the previous IRR. The IRRs that are marked as invalid, and their corresponding peak-to-peak and trough-to-trough intervals, are removed and the final time-domain estimation of the respiration rate is determined as the inverse of the average of the remaining (i.e. the valid) intervals. In the time-domain, the respiration rate 808 for the subject is determined to be 15.4 bpm.

FIG. 3($b$) illustrates a spectrum of the ECG signal showing the respiration rate in the frequency-domain. A search window 810 is determined based on the time-domain estimation of a respiration rate. The respiration rate 806 for the subject is then determined as the maximum frequency value (i.e. the R-wave amplitude) in the spectrum within the search window 810 based on the time-domain rate estimation. In this exemplary embodiment, the maximum frequency value in the spectrum within the search window 810 is 15 bpm. In other words, the respiration rate is determined in the frequency-domain to be 15 bpm. For example, as illustrated in FIG. 3($b$), the frequency-domain spectrum has a peak at 15 bpm and another peak at approximately 18 pbm. The rate estimate of 15.4 bpm from time-domain indicates that the peak at 15 bpm is to be determined as the respiration rate in the frequency-domain.

In other embodiments, instead of using the R-wave amplitude to determine the respiration rate, the embodiments involving an RS-range QRS-EDR signal processing algorithm use the RS-range to determine the respiration rate for the subject, and embodiments involving a HRV-EDR signal processing algorithm use the beat-to-beat interval to determine the respiration rate for the subject.

In some embodiments, a beat-to-beat irregularity in the ECG signal is also determined. A beat-to-beat irregularity may be determined using a trained Markov model to determine a Markov score. The input of this model can be an instant R-peak to R-peak interval of consecutive normal beats. For a segment of the ECG signal, if the smallest Markov score is less than a threshold value (for example, a value of −220), the segment is considered to have beat-tobeat irregularity and thus a HRV-EDR signal processing algorithm is not used for this segment.

In an embodiment that uses a VCG QRS-EDR signal processing algorithm, a multiple-channel ECG sensor (such as a 12-lead ECG sensor) and a lead transformation algorithm (such as the Frank VCG lead transformation algorithm) can be used to determine a cardiac electrical axis. Then, the R-peak QRS-EDR signal processing algorithm described above can be used to determine the respiration rate for the subject.

In embodiments in which the ECG signal is unevenly sampled, the ECG signal may first be processed to acquire an evenly sampled ECG signal. For example, the ECG signal may be interpolated and passed through a filter (such as a band-pass filter) to generate an evenly sampled ECG signal. Alternatively, an unevenly sampled ECG signal may be processed directly. For example, a least-squares spectral analysis LSSA (which may also be referred to as the Lomb or Lomb-Scargle method) may be used to determine a frequency spectrum directly on an unevenly sampled ECG signal. The frequency spectrum may then be used to identify a dominant frequency for the respiration rate.

In an embodiment that uses an EMG-EDR signal processing algorithm, the ECG signal may be sampled at a predefined rate (for example, 1000 sps) with a bandwidth up to a predefined value (for example, up to 500 Hz). A high pass filter (for example, at 250 Hz) may then be applied to accentuate the EMG and remove low frequency cardiac components. A root mean square (RMS) of the signal in a time window (for example, of 52 ms) is determined to obtain an RMS waveform. The time window may be a sliding window that slides forward by one sample at a time. Any unwanted residual QRS artefact can be removed based on a QRS complex detected using an ECG signal processing algorithm (for example, as described above) and linear interpolation. The RMS waveform is filtered (for example, using a low-pass or moving average filter) to smooth the RMS waveform. A spectral analysis is then performed to determine a respiration rate for the subject.

In an embodiment that uses an impedance signal processing algorithm or an embodiment that uses an accelerometer signal processing algorithm, a filter (such as a band-pass filter between 0.13 Hz and 0.50 Hz or similar) may be used to remove noise from an acquired impendence signal. A spectral analysis may then be performed to determine the respiration rate of the subject.

In an embodiment that uses a PPG signal processing algorithm, the respiration information in the PPG signal is reflected as the cyclic modulation on the PPG signal. The determination of respiration information from a PPG signal is similar to the determination of the QRS complex in an ECG signal in that an envelope of the PPG signal is detected. The detected envelope of the PPG signal is then used to determine the respiration rate of the subject. Specifically, the peak amplitude of each beat in the PPG signal is determined and then an interpolation algorithm is used to generate an evenly sampled waveform envelope. A spectral analysis may then be performed on the evenly sampled waveform envelope to determine the respiration rate of the subject.

Although example signal processing algorithms have been provided, it will be understood that other signal processing algorithms that are suitable for determining respiration information from a physiological signal can also be used.

In some embodiments, respiratory information for the subject is determined by processing each of the one or more physiological signals using at least one respective signal processing algorithm. For example, for each of the one or more physiological signals, respiratory information for the subject may be determined by processing the physiological signal using one or more signal processing algorithms selected for that physiological signal. In other words, there may be a one-to-one correspondence between a physiological signal and a signal processing algorithm used to process the physiological signal. However, in other embodiments, this one-to-one correspondence is not present.

For example, in other embodiments, respiratory information for the subject is determined by processing each of the one or more physiological signals using any one or more of the selected signal processing algorithm. For example, respiratory information for the subject may be determined by processing at least one of the one or more physiological signals using any one of the selected signal processing algorithms or using a plurality of the selected signal processing algorithms. In this way, the same signal processing algorithm may be used to process more than one physiological signal and, similarly, more than one signal processing algorithm may be used to process the same physiological signal.

In other embodiments, respiratory information for the subject is determined by processing each of the one or more physiological signals using each selected signal processing algorithm. For example, respiratory information for the subject may be determined by processing all physiological signals using all selected signal processing algorithms.

In embodiments in which two or more signal processing algorithms are selected for at least one physiological signal, prior to determining respiratory information for the subject (at block 208), the two or more signal processing algorithms selected for the at least one physiological signal may be combined into a combined signal processing algorithm. According to these embodiments, respiratory information for the subject may then be determined based on the at least one physiological signal using the combined signal processing algorithm for the at least one physiological signal.

In some embodiments, the combining of two or more (i.e. a plurality of) signal processing algorithms may comprise combining different signal processing algorithms to determine respiratory information for the subject from the same physiological signal or from different physiological signals. For example, this may involve spectrally processing an output (for example, a waveform) of different signal processing algorithms to obtain a combined cross-spectrum.

Figure 4:
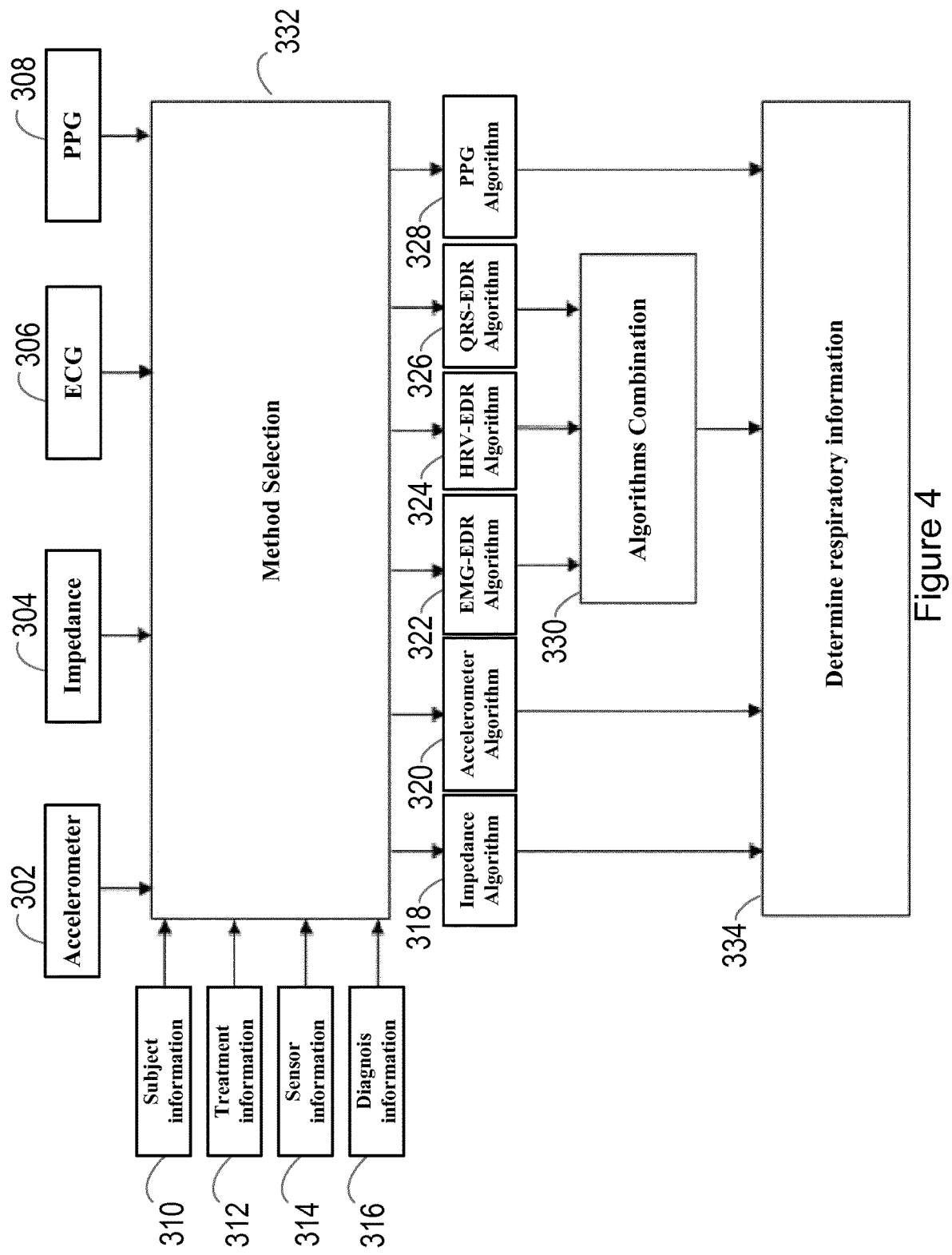
FIG. 4 is a flow chart illustrating a method according to an exemplary embodiment for combining signal processing algorithms.

FIG. 4 is a flow chart illustrating an exemplary embodiment in which different signal processing algorithms are combined to determine respiratory information for the subject from different physiological signals in this way. Specifically, according to this exemplary embodiment, different signal processing algorithms are used at blocks 318, 320, 322, 324, 326 and 328 to determine respiratory information for the subject from different physiological signals acquired at blocks 302, 304, 306 and 308.

A plurality of physiological signals are acquired (at blocks 302, 304, 306 and 308). According to this exemplary embodiment, an accelerometer signal is acquired at block 302, an impedance signal is acquired at block 304, an ECG signal is acquired at block 306, and a PPG signal is acquired at block 308. Also, contextual information relating to the subject and the physiological signals is obtained (at blocks 310, 312, 314 and 316). According to this exemplary embodiment, the contextual information includes subject information acquired at block 310, treatment information acquired at block 312, sensor information acquired at block 314, and diagnosis information acquired at block 316.

At block 332, a plurality of signal processing algorithms are selected for each physiological signal acquired at blocks 302, 304, 306 and 308 based on the contextual information acquired at blocks 310, 312, 314 and 316. Specifically, according to this exemplary embodiment, an impedance signal processing algorithm is output at block 318, an accelerometer signal processing algorithm is output at block 320, an EMG-EDR signal processing algorithm is output at block 322, a HRV-EDR signal processing algorithm is output at block 324, a QRS-EDR signal processing algorithm is output at block 326 and a PPG signal processing algorithm is output at block 328.

At block 330, three of the signal processing algorithms are combined into a combined signal processing algorithm. Specifically, the EMG-EDR signal processing algorithm, the HRV-EDR signal processing algorithm, and the QRS-EDR signal processing algorithm are combined into a combine signal processing algorithm.

For example, each of these three signal processing algorithms can be used to generate a waveform (represented by A, B, and C) with the same sample rate. A spectral analysis algorithm (such as fast Fourier transform algorithm FFT, window-based periodogram, or another spectral density estimation algorithm) can then be used to determine an individual power spectrum for each waveform denoted as $A_n e^{i\phi_{A,n}}$, $B_n e^{i\phi_{B,n}}$, and $C_n e^{i\phi_{C,n}}$. Here, n is the index of a frequency point in the waveforms, $A_n$, $B_n$, and $C_n$ are the amplitudes of the waveforms, and $\phi_{A,n}$, $\phi_{B,n}$, and $\phi_{C,n}$ are the waveform phases. The signal processing algorithms can be combined by determining a cross spectrum as $A_n B_n C_n e^{i(\phi_{A,n}-\phi_{B,n}-\phi_{C,n})}$. The amplitude of the cross spectrum is the multiplication of the individual amplitudes of the waveforms. This amplitude of the cross spectrum can then be analysed to determine respiratory information for the subject. For example, a respiration rate for the subject may be determined as the dominant frequency in the cross spectrum.

At block 334, respiratory information for the subject is determined based on the physiological signals acquired at blocks 302, 304, 306 and 308 using the impedance signal processing algorithm output at block 318, the accelerometer signal processing algorithm output at block 320, the combined signal processing algorithm at block 330, and the PPG signal processing algorithm output at block 328.

Figure 5:
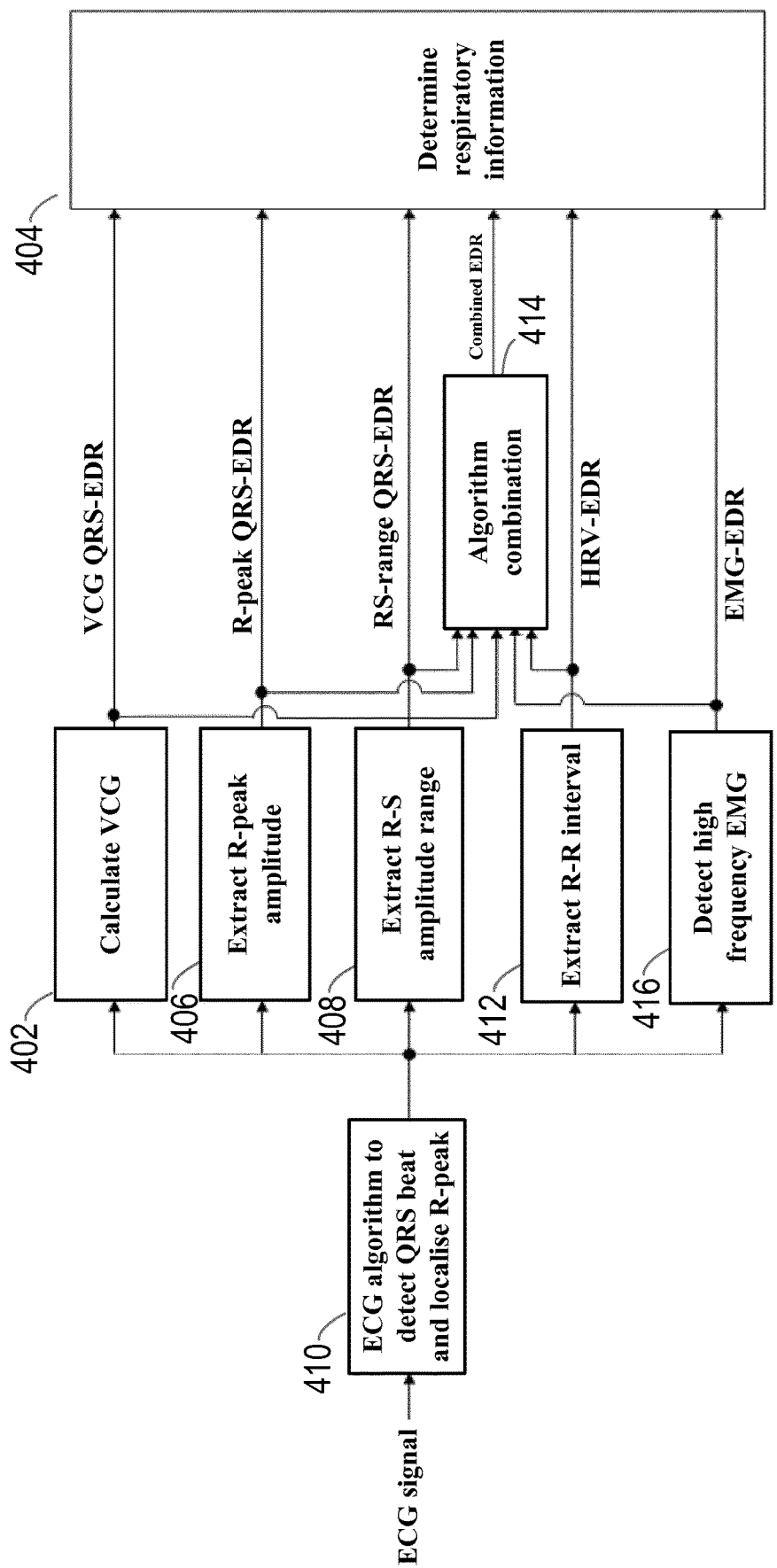
FIG. 5 is a flow chart illustrating a method according to another exemplary embodiment for combining signal processing algorithms.

FIG. 5 is a flow chart illustrating an exemplary embodiment in which different signal processing algorithms are combined to determine respiratory information for the subject from the same physiological signal. Specifically, according to this exemplary embodiment, different electrocardiogram (ECG) signal processing algorithms are used to determine respiratory information for the subject from the same physiological signal and the different signal processing algorithms are also combined to determine respiratory information for the subject from the same physiological signal.

An electrocardiogram (ECG) signal is first acquired. The ECG signal may be acquired from a single channel ECG sensor or a multi-channel ECG sensor. At block 410, an initial ECG signal processing algorithm is used to detect characteristics in the acquired ECG signal. For example, a QRS beat is detected and an R-peak in the acquired ECG signal is localised. Then, a plurality of ECG signal processing algorithms are used to process the acquired ECG signal. A VCG QRS-EDR signal processing algorithm is used to calculate a VCG at block 402, an R-peak QRS-EDR signal processing algorithm is used to extract an amplitude of the R-peak at block 404, an RS-range QRS-EDR signal processing algorithm is used to extract the RS amplitude range at block 408, a HVR-EDR signal processing algorithm is used to extract the interval between R-peaks (which can be referred to as the R-R interval) at block 412, and an EMG-EDR signal processing algorithm is used to detect high frequency EMG at block 416. Also, each of the ECG signal processing algorithms of blocks 402, 406, 408, 412 and 416 are combined into a combined ECG signal processing algorithm (which can be referred to as Combined-EDR). The different ECG signal processing algorithms may be combined using a cross spectrum, as described earlier.

At block 404, respiratory information for the subject is determined based on the acquired ECG signal from the output of each of the VCG QRS-EDR signal processing algorithm at block 402, the R-peak QRS-EDR signal processing algorithm at block 404, the RS-range QRS-EDR signal processing algorithm at block 408, the HVR-EDR signal processing algorithm at block 412, the EMG-EDR signal processing algorithm at block 416 and the combined signal processing algorithm at block 414.

Figure 6:
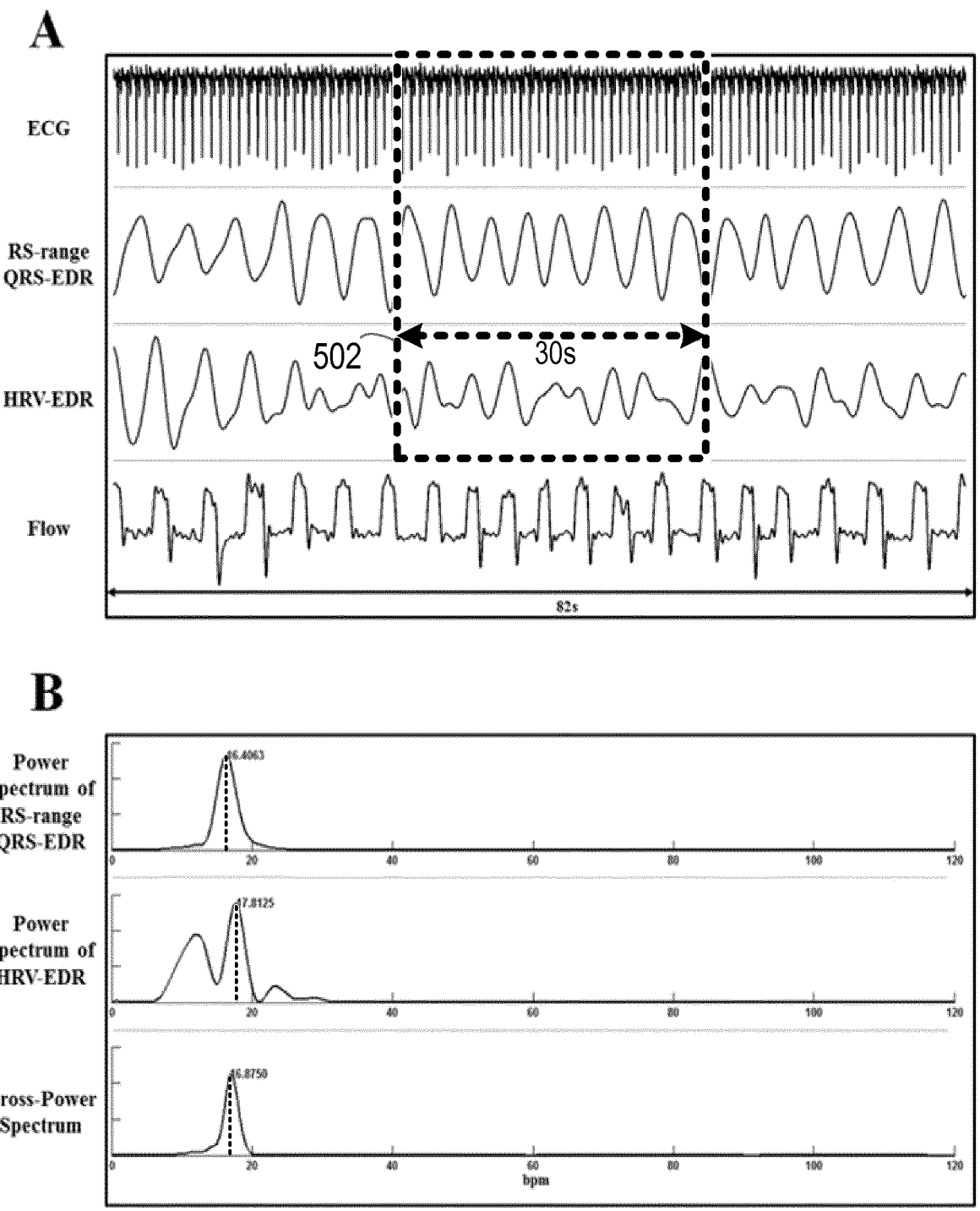
FIG. 6 is a graphical illustration of signal processing algorithm outputs according to an embodiment.

FIG. 6 is a graphical illustration of different example waveforms output by processing the same ECG signal using different signal processing algorithms.

FIG. 6A illustrates example output waveforms from a single-channel ECG sensor by processing the acquired ECG signal from the sensor using the RS-range QRS-EDR signal processing algorithm and the HRV-EDR signal processing algorithm. The example flow waveform shown in FIG. 6A is an airflow signal acquired by direct monitoring of the respiration of the subject (for example, using a nasal cannula).

FIG. 6B illustrates an example of a determination of the respiration rate of the subject based on a spectral analysis of a 30-second segment window 502 in FIG. 6A. An individual power spectrum for the output waveform from the QRS-EDR signal processing algorithm and the output waveform from the HRV-EDR signal processing algorithm are determined (for example, using a Blackman-window based periodogram). A correlated cross-power spectrum is also determined. It can be seen that the cross-power spectrum provides a more robust way to estimate the dominant frequency and thus identify the respiration rate for the subject than the individual power spectrums.

In embodiments in which two or more physiological signals are acquired, the respiratory information that is determined from each of the two or more physiological signals may be combined. The respiratory information for the subject may be determined using the same signal processing algorithms for at least two (or all) of the two or more physiological signal, or using different signal processing algorithms for at least two (or all) of the two or more physiological signal.

Figure 7:
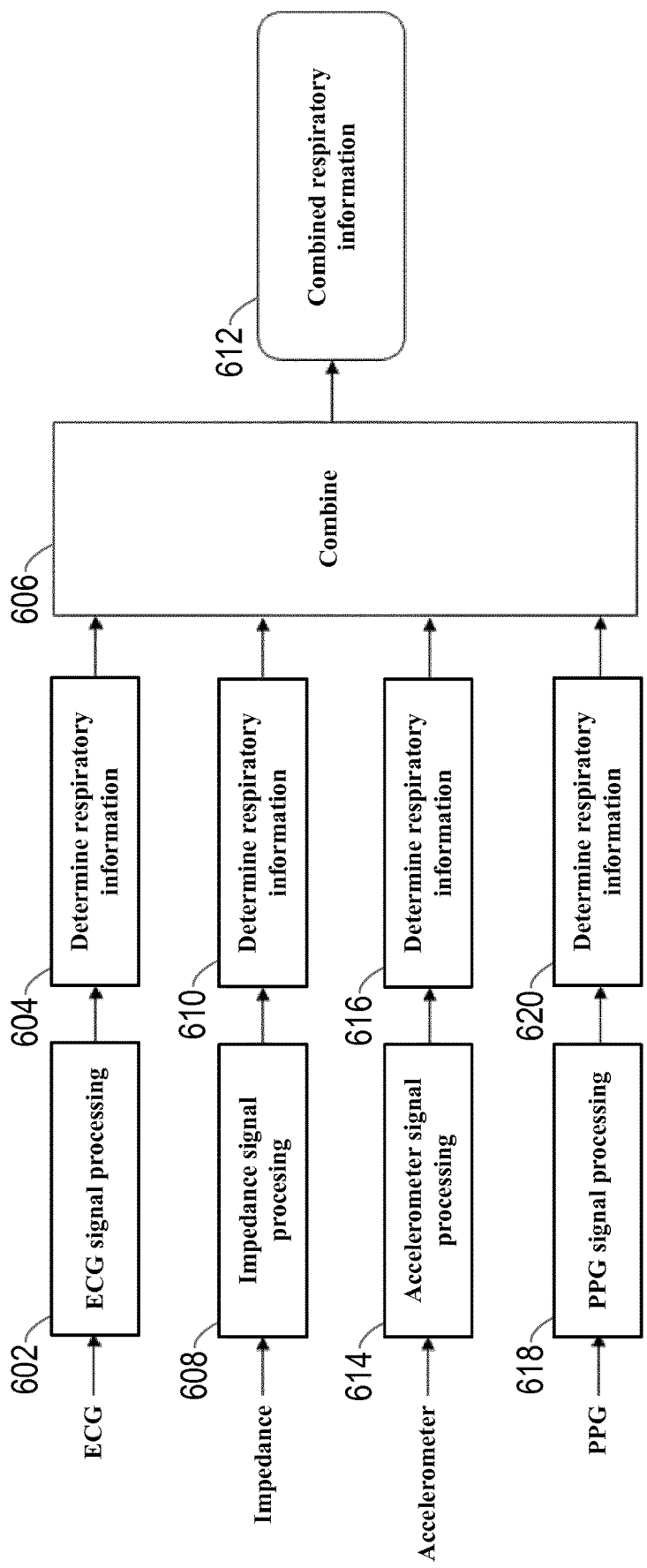
FIG. 7 is a flow chart illustrating an exemplary embodiment for combining respiratory information.

FIG. 7 is a flow chart illustrating an exemplary embodiment in which respiratory information for the subject determined from different physiological signals using different signal processing algorithms is combined. Specifically, according to this exemplary embodiment, different signal processing algorithms are used at blocks 602, 608, 614 and 618 to determine respiratory information for the subject from different physiological signals.

A plurality of physiological signals are acquired, a corresponding signal processing algorithm is selected for each acquired physiological signal and the acquired physiological signals are processed using the corresponding signal processing algorithm. According to this exemplary embodiment, an ECG signal is acquired and processed using an ECG signal processing algorithm at block 602, an impedance signal is acquired and processed using an impedance signal processing algorithm at block 608, an accelerometer signal is acquired and processed using an accelerometer signal processing algorithm at block 614, and a PPG signal is acquired and processed using a PPG signal processing algorithm at block 618.

At blocks 604, 610, 616, and 620, respiratory information for the subject is determined based on each of the physiological signals using the output from the corresponding signal processing algorithm selected for that physiological signal. Specifically, according to this exemplary embodiment, respiratory information for the subject is determined based on the ECG signal using the output from the ECG signal processing algorithm at block 604, respiratory information for the subject is determined based on the impedance signal using the output from the impedance signal processing algorithm at block 610, respiratory information for the subject is determined based on the accelerometer signal using the output from the accelerometer signal processing algorithm at block 616, and respiratory information for the subject is determined based on the PPG signal using the output from the PPG signal processing algorithm at block 620.

At block 606, the respiratory information determined from each of the acquired physiological signals using each of the different signal processing algorithms at blocks 604, 610, 616, and 620 is combined. At block 612, the combined respiratory information is output.

Each respiration rate that is determined may be quantified into a numerical value. The output of the combined respiration information may be a weighted sum of each of the respiration rate values. The weight for each respiration rate value may be determined based on the quality of the physiological signal from which that respiration rate is determined. For example, a signal quality level may be provided for each physiological signal. The signal quality level may be marked as Poor (P), Moderate (M), or Good (G). The physiological signals with P quality are assigned weight 0. In other words, the physiological signals with P quality are excluded from the combination process at block 606. The physiological signals with quality level G are assigned a weight twice that of the physiological signals with quality level M. If there are $n_M$ physiological signals with quality level M, and $n_G$ physiological signals with quality level G, the weight for each physiological signal with quality level M is then $w=1/(n_M+2*n_G)$, and the weight for each physiological signal with quality level G is $2*w$.

Figure 8:
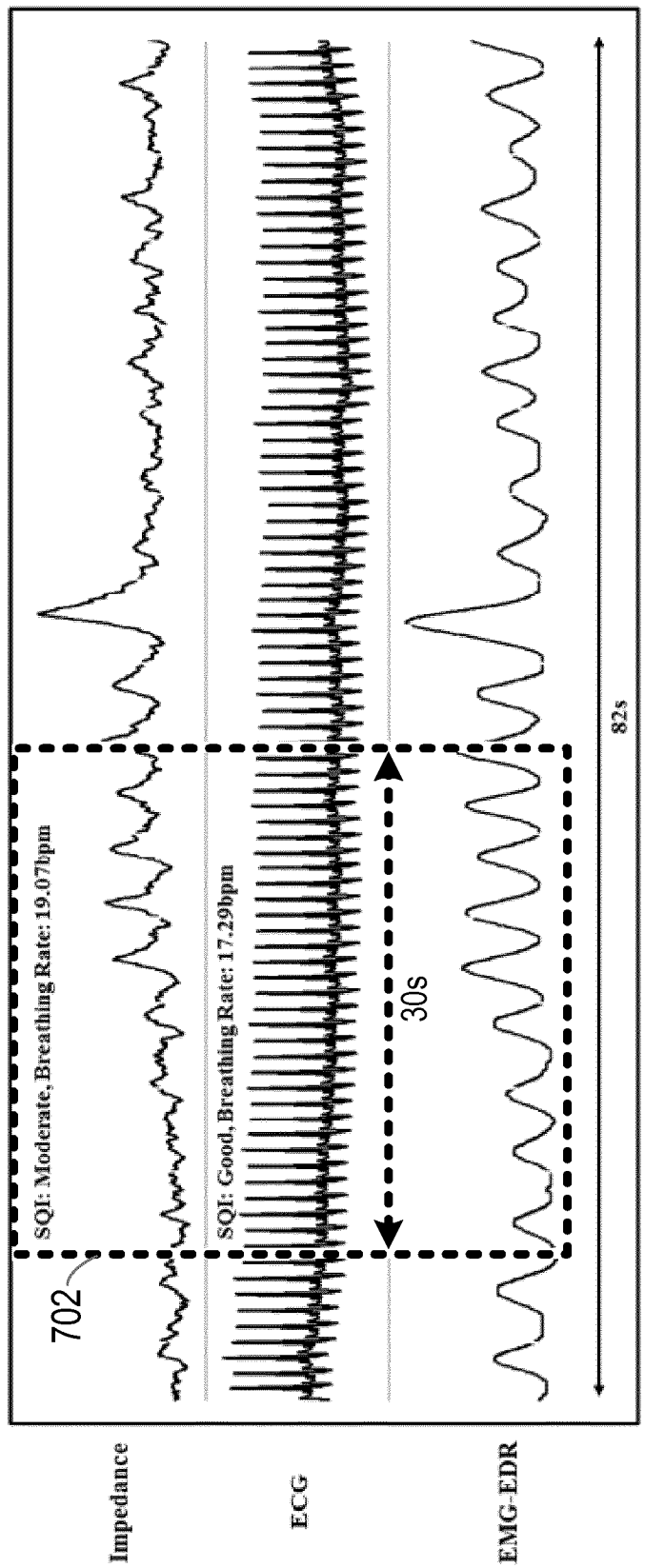
FIG. 8 is a graphical illustration of signal processing algorithm outputs according to an embodiment.

FIG. 8 is a graphical illustration of different example waveforms output by processing multiple different physiological signals using different signal processing algorithms.

In this example, both impedance and ECG signals are available and can each be used to determine respiration information for the subject. The quality level for the impedance signal is Moderate (M) and the quality level for ECG signal is Good (G). A respiration rate for the subject determined from the ECG signal and the impedance signal are 19.07 bpm and 17.29 bpm, respectively. The respiration rate determined from the impedance signal is assigned a weight of ⅓ and the respiration rate determined from the ECG signal is assigned the weight of ⅔. Therefore, the combined respiration rate for the subject is $(1*19.07+2*17.29)/3=17.88$ bpm.

Other techniques for combining respiration information determined from different signal processing algorithms can also be used. For example, an adaptive signal processing model may be used in which one source of respiration information is used as a reference signal. In one embodiment, an ECG signal may be used as the reference signal and an impedance signal may be used as a desired signal. The ECG signal and the impedance signal may be input into an adaptive filter and the respiration information for each signal determined. The respiration information determined based on the ECG signal and the respiration information determined based on the impedance signal are then combined to determine combined respiration information. Although an example has been provided here for combining respiration information, it will be understood that respiration information determined from any physiological signals can be combined in this way.

Although examples have been provided for the signal processing algorithms, the way in which signal processing algorithms can be combined and the way in which determined respiration information can be combined, it will be understood that other signal processing algorithms and combination techniques can also be used.

There is therefore provided an improved method and apparatus for determining respiratory information for a subject. The method and apparatus can be useful in providing reliable and accurate non-invasive monitoring of respiratory activity in the home of the subject or in a professional healthcare facility (such as a hospital). The method and apparatus can be applied in a wearable device, an exercise device, an ambulatory device, a bed-side monitoring device, a telemetry device, a life support device or any other device that acquires at least one physiological signal of a subject.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of operating an apparatus comprising a control unit to determine respiratory information for a subject, the method comprising: acquiring, by the control unit, one or more physiological signals indicative of at least one physiological characteristic of the subject; obtaining, by the control unit, contextual information relating to at least one of the subject and the one or more physiological signals; selecting, by the control unit, based on the contextual information, at least one signal processing algorithm for each of the one or more physiological signals, the at least one signal processing algorithm being adapted to determine respiratory information, wherein selecting at least one signal processing algorithm is further based on a set of rules relating to an advantage or disadvantage of each of a plurality of signal processing algorithms utilized for inclusion or exclusion: and determining, by the control unit, respiratory information for the subject based on the one or more physiological signals using the at least one signal processing algorithm selected for the one or more physiological signals.

2. A method as claimed in claim 1, wherein the one or more physiological signals for which at least one signal processing algorithm is selected are one or more physiological signals selected based on the contextual information relating to the one or more physiological signals.

3. A method as claimed in claim 1, wherein two or more signal processing algorithms are selected for at least one physiological signal and the method further comprises:

combining, by the control unit, the two or more signal processing algorithms selected for the at least one physiological signal into a combined signal processing algorithm; and determining, by the control unit, respiratory information for the subject based on the at least one physiological signal using the combined signal processing algorithm for the at least one physiological signal.

4. A method as claimed in claim 1, wherein two or more physiological signals are acquired and the method further comprises:

combining, by the control unit, the respiratory information that is determined from each of the two or more physiological signals.

5. A method as claimed in claim 1, further comprising:

prior to determining respiratory information for the subject, filtering the one or more physiological signals to remove noise.

6. A method as claimed in claim 1, wherein the respiratory information comprises at least one of a respiration rate for the subject and a breathing pattern for the subject.

7. A method as claimed in claim 1, wherein the at least one signal processing algorithm selected for the physiological signal comprises one or more of:

a frequency domain analysis of the physiological signal;
a time domain analysis of the physiological signal; and
an auto-regression analysis of the physiological signal.

8. A method as claimed in claim 1, further comprising: outputting the determined respiratory information for the subject.

9. A method as claimed-in claim 1, further comprising:

determining, by the control unit, a respiratory condition for the subject based on the determined respiratory information for the subject.

10. A method as claimed in claim 9, further comprising:

outputting, by the control unit, the determined respiratory condition for the subject.

11. A non-transitory computer program product comprising a computer readable medium, the computer readable medium having computer readable code embodied therein, the computer readable code being configured such that, on execution by a suitable computer or processor, the computer or processor is caused to perform the method of claim 1.

12. An apparatus for determining respiratory information for a subject, the apparatus comprising: a control unit configured to: acquire one or more physiological signals indicative of at least one physiological characteristic of the subject; obtain contextual information relating to at least one of the subject and the one or more physiological signals; select, based on the contextual information, at least one signal processing algorithm for each of the one or more physiological signals, the at least one signal processing algorithm being adapted to determine respiratory information, wherein selecting at least one signal processing algorithm is further based on a set of rules relating to an advantage or disadvantage of each of a plurality of signal processing algorithms utilized for inclusion or exclusion: and determine respiratory information for the subject based on the one or more physiological signals using the at least one signal processing algorithm selected for the one or more physiological signals.

13. An apparatus as claimed in claim 12, wherein the control unit is configured to acquire the one or more physiological signals by controlling one or more physiological sensors to acquire the one or more physiological signals.

14. An apparatus as claimed in claim 13, wherein the one or more physiological sensors comprise at least one of: an electrocardiogram sensor, an impedance sensor, an acceleration sensor, and a photoplethysmography sensor.

15. An apparatus as claimed in claim 13, wherein a wearable device comprises the one or more physiological sensors.

16. An apparatus as in claim 12, the control unit further configured to: output the determined respiratory information for the subject.

17. An apparatus as in claim 12, the control unit further configured to:

determine a respiratory condition for the subject based on the determined respiratory information for the subject.

18. An apparatus as in claim 17, the control unit further configured to:

output the determined respiratory condition for the subject.

* * * * *